United States Patent [19]

Mowery, Jr.

[11] Patent Number: 4,861,555
[45] Date of Patent: Aug. 29, 1989

[54] APPARATUS FOR CHROMATOGRAPHIC ANALYSIS OF IONIC SPECIES

[75] Inventor: Richard A. Mowery, Jr., Bartlesville, Okla.

[73] Assignee: Applied Automation, Inc., Bartlesville, Okla.

[21] Appl. No.: 710,780

[22] Filed: Mar. 11, 1985

[51] Int. Cl.$^4$ .................. G01N 30/02; G01N 30/96
[52] U.S. Cl. .................. 422/70; 73/61.1 C; 210/198.2; 210/656; 204/149; 204/180.1; 204/182.4; 204/272; 436/150; 436/161; 436/175; 436/177
[58] Field of Search .................. 422/68, 69, 70; 436/150, 161, 175, 176, 177, 178; 73/61.1 C; 210/198.2, 649, 656, 659; 204/149, 182.4, 180.1, 272, 299 EC, 301

[56] References Cited

U.S. PATENT DOCUMENTS

| | | | |
|---|---|---|---|
| 2,938,849 | 5/1960 | Stoddard | 204/182.4 X |
| 3,074,865 | 1/1963 | Gaysowski | 204/301 X |
| 3,129,152 | 4/1964 | Teske et al. | 204/128 |
| 3,193,484 | 7/1965 | Gleim et al. | 204/79 |
| 3,222,267 | 12/1965 | Tirrell et al. | 204/301 X |
| 3,326,785 | 6/1967 | Williams | 204/272 |
| 3,341,299 | 9/1967 | Catravas | 422/70 X |
| 3,399,972 | 9/1968 | Skeggs et al. | 422/70 X |
| 3,506,562 | 4/1970 | Coackley | 204/149 |
| 3,666,652 | 5/1972 | Krauer | 204/195 |
| 3,718,556 | 2/1973 | Rohrback | 204/149 |
| 3,920,397 | 11/1975 | Small et al. | 23/230 |
| 3,926,559 | 12/1975 | Stevens | 23/230 |
| 4,248,681 | 2/1981 | Sweeny | 204/103 |
| 4,265,634 | 5/1981 | Pohl | 23/230 |
| 4,312,715 | 1/1982 | Abery et al. | 204/1 T |
| 4,314,823 | 2/1982 | Rich, Jr. et al. | 23/230 |
| 4,403,039 | 9/1983 | Ban et al. | 436/150 |
| 4,459,357 | 7/1984 | Jansen et al. | 436/161 |
| 4,487,670 | 12/1984 | Bellanger et al. | 204/149 X |

FOREIGN PATENT DOCUMENTS

| | | | |
|---|---|---|---|
| 2559037 | 7/1977 | Fed. Rep. of Germany | 204/180 R |
| 2308857 | 11/1976 | France | 204/149 |
| 0189090 | 11/1983 | Japan | 204/149 |

OTHER PUBLICATIONS

Ellis, "Fresh Water from the Ocean", pp. 42-61, The Ronald Press Co., New York, 1954.
Lingane, J. J., *Electroanalytical Chemistry*, 2nd ed., Interscience Publishers, Inc., New York, 1958, pp. 207-211.
Bouyoucos, S. A., "Determination of Organic Antons by Ion Chromatography Using a Hollow Fiber Suppressor", *Journal of Chromatography*, 242 (1982) pp. 170-176.

*Primary Examiner*—Robert J. Hill, Jr.
*Attorney, Agent, or Firm*—Laney, Dougherty, Hessin & Beavers

[57] ABSTRACT

An apparatus and method for the ion chromatographic analysis of ionic species of a common first polarity opposite to a second polarity employ an eluant ion suppressor cell having two electrodes. The ionic species to be analyzed and an eluant solution are introduced in solution to an ion exchange resin bed. The eluant solution essentially consists of an eluting reagent in solution such that the eluting reagent is ionized to form first eluant ions of the first polarity and second eluant ions of the second polarity. An effluent essentially consisting of separated ionic species, first eluant ions and second eluant ions in solution is discharged from the resin bed. The effluent is introduced through an inlet in the suppressor cell such that the effluent flows along a surface of the first and second electrodes. An electrical voltage is applied to the electrodes so as to maintain the first electrode at the first polarity and the second electrode at the second polarity. Furthermore, the voltage is maintained at a level sufficient to substantially neutralize first eluant ions flowing along the second electrode surface. Effluent portions flowing closely adjacent to the first and second electrode surfaces are passed out respective first and second outlets which are located downstream from the cell inlet. Effluent flowing from the second cell outlet is passed to a detector which detects the ionic species.

6 Claims, 2 Drawing Sheets

APPARATUS FOR CHROMATOGRAPHIC ANALYSIS OF IONIC SPECIES

BACKGROUND OF THE INVENTION

This invention relates to an apparatus for the ion exchange chromatographic analysis of ionic species, wherein an eluant ion suppressor cell is employed. In another aspect, the invention relates to a method for the ion exchanged chromatographic analysis of ionic species.

In recent years, a form of chromatography called "ion chromatography" has developed. It has been used for the laboratory analysis of inorganic compounds suitably ionized in solution. Reference is made to U.S. Pat. No. 3,920,397 and other patents assigned to the Dow Chemical Company for descriptions of prior art ion chromatography systems.

In such prior ion chromatography systems, ionic species to be analyzed are introduced in solution to a separation column which contains an ion exchange resin. Also introduced to the separation column is a flow of eluant solution which acts as a carrier for the ionic species. Within the resin bed, ions in the eluant solution act to displace ionic species ions which have become bound to the resin bed at ion exchange sites. The separation column discharges an effluent which contains separated ionic species. As used herein, "separated" means that the ionic species appear at different times in the effluent, i.e., the species are resolved. In addition to the separated ionic species, however, the effluent also contains eluant solution ions. These eluant ions act essentially as background noise, and tend to cover up the ionic species of interest, making the ionic species barely detectable. Thus, a suppressor column is typically included to neutralize the eluant ions. The suppressor column also includes an ion exchange resin bed which neutralizes the eluant ions so as to convert the eluant solution to weakly ionized form. The fluid discharged from the suppressor column is then passed to a suitable detector, such as a conductivity detector, which detects the ionic species.

The most serious problem in the above described ion chromatography system resides in the suppressor column. The resin bed in the suppressor column after a period of time becomes "spent", and must be replaced or regenerated. This regeneration typically involves soaking the resin bed in a strong mineral acid or a strong base. Such periodic regeneration or replacement is time consuming and expensive.

Another problem associated with the suppressor column is its tendency to add to the "void" volume of the chromatography system. As used herein, void volume refers to the volume through which the separated ionic species must flow. Such void volume tends to spread the ions, thus resulting in band spreading or spreading of peaks obtained in the readout equipment. Each peak corresponds to a particular ionic species. As with any detection apparatus, it is always desirable to obtain the sharpest peaks possible. The suppressor column, therefore, tends to cause undesirable band spreading due to its significant addition to the void volume of the system.

THE SUMMARY OF THE INVENTION

It is, therefore, an object of the invention to provide an apparatus and method for the ion exchange analysis of ionic species.

It is also an object of the invention to provide an apparatus and method for the ion exchange analysis of ionic species which employ a means for suppressing eluant ions which does not require regeneration or replacement.

It is yet another object of the invention to provide an apparatus and method for the ion chromatographic analysis of ionic species having the capability of suppressing eluant ions, and wherein band spreading is minimized.

The above objects are realized in an apparatus and method for the ion chromatographic analysis of ionic species of a common polarity which employs an eluant ion suppressor cell with two electrodes. For the purpose of this description, each ionic species will be assumed to be charged according to a first polarity, wherein the first polarity is opposite to a second polarity. The ionic species to be analyzed and an eluant solution are introduced in solution to an ion exchange resin bed. The eluant solution essentially consists of an eluting reagent in solution such that the eluting reagent is ionized to form first eluant ions of the first polarity and second eluant ions of the second polarity. An effluent essentially consisting of separated ionic species, first eluant ions and second eluant ions in solution is discharged from the resin bed. The effluent is introduced through an inlet in the suppressor cell such that the effluent flows along a surface of the first electrode and a surface of the second electrode. An electrical voltage is applied to the electrodes so as to maintain the first electrode at the first polarity and the second electrode at the second polarity. Furthermore, the voltage is maintained at a level sufficient to substantially neutralize first eluant ions flowing along the second electrode surface. Effluent portions flowing closely adjacent to the first and second electrode surfaces are passed out respective first and second outlets which are located downstream from the cell inlet. Effluent flowing from the second cell outlet is passed to a detector which detects the ionic species.

Therefore, eluant of ions having the same polarity as the ionic species of interest are attracted to a common electrode, and these particular eluant ions are neutralized by the electrode. Since these eluant ions are neutralized, they do not interfere with the detection of the ionic species. The other and oppositely charged eluant ions flow along the other electrode and pass out the other outlet accordingly for disposal or other appropriate use.

According to a preferred embodiment, one of the first or second electrodes comprises a hollow electrically conductive member and the other electrode comprises a tubular member disposed generally coaxially within the hollow member. The cell inlet is defined by a passage through a wall of the hollow member, and one of the cell outlets is also defined by a passage through a wall of the hollow member. An open end of the tubular member serves as the other cell outlet. Preferably, the eluting reagent is an acid if the ionic species being detected are positive. If the ionic species being detected are negative, the eluting reagent is preferably a base.

Unlike prior ion exchange chromatography systems, the present apparatus and method utilize a suppressor cell which does not require periodic replacement or regeneration. Furthermore, the ionic species tend to be attracted to the surface of one of the electrodes so as to flow closely adjacent to that surface. The ionic species therefore flow in the cell through a very small volume, thus reducing the void volume and minimizing band spreading.

DESCRIPTION OF THE PREFERRED EMBODIMENTS

Figure 1:
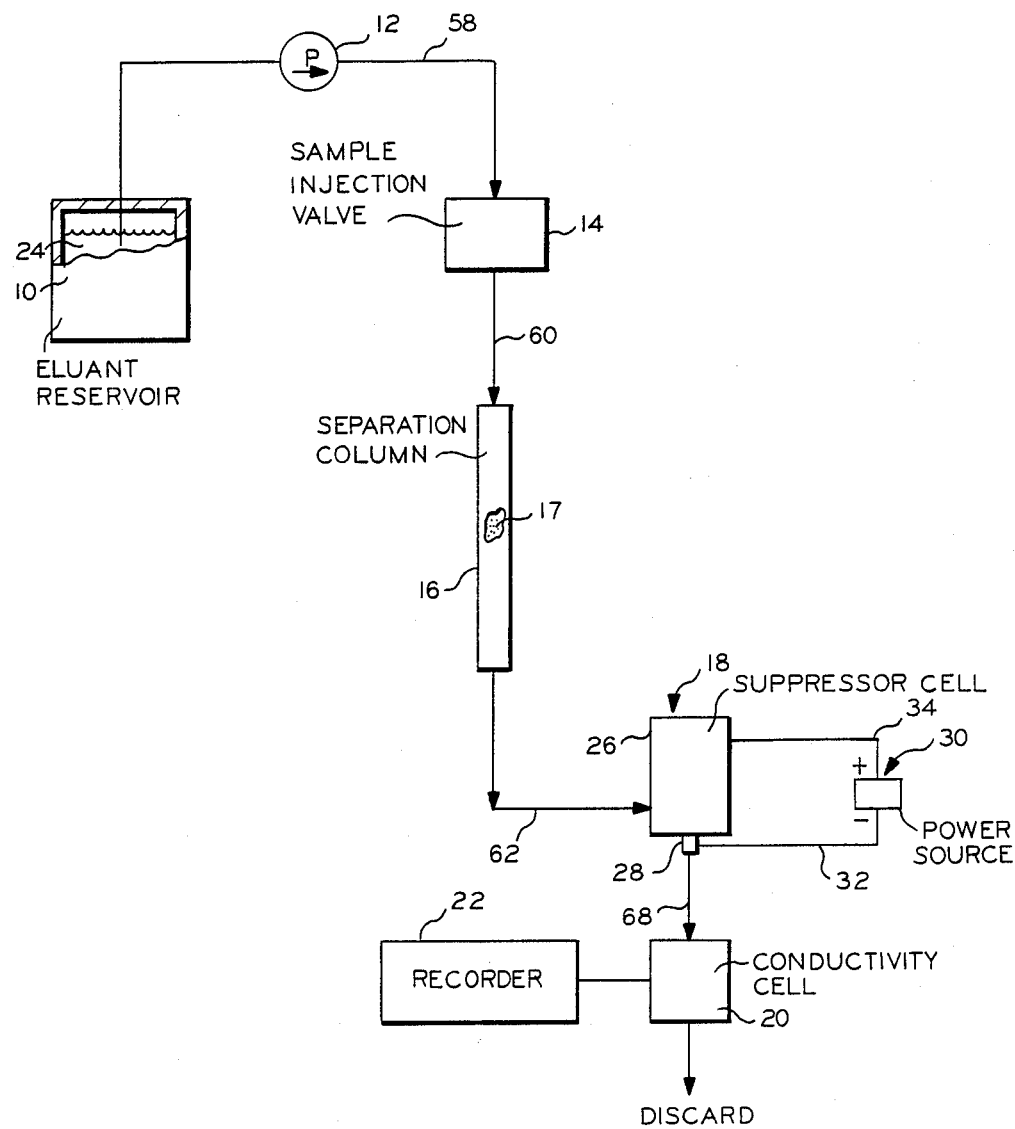
FIG. 1 is a schematic representation of one embodiment of an apparatus for use in the analysis of positively charged ionic species. The apparatus includes a suppressor cell for neutralizing certain eluant ions so as to minimize background noise.

Referring to FIG. 1, the illustrated apparatus is set up for the detection of positively charged ionic species, as noted above. It should be understood that an apparatus constructed according to the invention should be prearranged, as will be discussed further below, to detect either positive or negative ionic species.

The apparatus shown in FIG. 1 essentially includes the following elements arranged in series such that the outlet of one element is connected to the inlet of the next element: an eluant reservoir 10; a pump 12; a sample injection valve 14; a separation column 16; an eluant ion suppressor cell 18; and a conductivity cell 20. A recorder 22 can also be provided to receive signals from conductivity cell 20 and to record those signals in any convenient manner for future reference.

A portion of eluant reservoir 10 has been broken away to reveal eluant solution 24 contained therein. Eluant solution 24 includes an eluting reagent suitably dissolved in a solvent. The eluant solution should be capable of moving the most tightly bound species of interest on the resin bed in separation column 16. To that end it is preferred in this particular embodiment to employ an acid, particularly a strong mineral acid, as the eluting reagent. Suitable eluting reagents include HCl, $HNO_3$, $H_2SO_4$ and $H_3PO_4$. The most preferred solvent is pure water, but a mixture of water and another ingredient such as methanol or acetone could be utilized. In any event, it is preferably that the eluting reagent be in aqueous solution. The concentration of the eluting reagent is generally in the range of about 0.0001 to about 0.01 normal, the more concentrated solution being useable to move the more tightly bound ions on the resin. A highly concentrated solution will reduce the time required to move a sample through the apparatus, but will provide a greater degree of background noise. Thus a concentration is typically selected which will give a suitable sample residence time and separation as well as an acceptably low level of background noise.

Sample injection valve 14 is of the type now commonly used for chromatographic analyses and typically is provided with several bores in the valve core of different volumes or void spaces. These bores are adapted for holding a sample to be analyzed. The sample holding volume is typically filled by a syringe or other convenient means after which the valve is manipulated to bring the sample holding volume into series with a stream of eluant solution which is constantly passing through a portion of the valve body.

Separation column 16 typically includes a hollow cylindrical member which contains a suitable ion exchange resin bed therein. A portion of the cylindrical member is broken away to reveal resin bed 17 therein. The ion exchange resin utilized should be capable of separating a plurality of ionic species on being added to and eluted from the resin bed end column 16. In addition, the ion exchange resin is selected to achieve good separation with the particular eluting reagent employed. The resin is preferably one with high performance characteristics in its ability to separate ionic species, but at the same time is a resin of low specific capacity so that only a small amount of eluting reagent is needed to accomplish separation and elution of the resin bed. For high performance characteristics it is essential that highly active ion exchange sites are disposed on and in a surface layer of the resin beads or particles and that such sites be readily and promptly available to ionic species in solution flowing over the resin bead surfaces. Therefore, the preferred separator resin is pellicular in nature in having the active sites at or very close to the surfaces of the resin beads. Although less preferred, gel particle resins could also be used.

One very effective ion exchange resin for use in the separation of positively charged, or cationic, species in the FIG. 1 apparatus is a surface sulfonated copolymer of styrene and divinyl benzene. The beads are preferably of an average particle size in the range of about 200 to about 400 mesh although finer sizes may be used. For a detailed description of a process of making such a resin, reference is made to U.S. Pat. No. 3,920,397. Silica based ion exchange resins in the range of 5 $\mu m$ to 10 $\mu m$ can also be used.

Suppressor cell 18 includes an electrode 26 and an electrode 28 mounted within and insulated from electrode 26 in a manner described in detail with reference to FIG. 2. Also providing is an adjustable DC power source 30 having a negative terminal connected to electrode 28 via lead line 32, and a positive terminal connected to electrode 26 through line 34. Power source 30 is preferably adjustable, such that the voltage and current supplied to the electrodes can be readily adjusted.

Conductivity cell 20 is of conventional design, and produces an electrical signal proportional to the amount of ionic material flowing therethrough. The conductivity cell is employed in the illustrated embodiment because of its extreme sensitivity. However, other detectors could be used such as a polarographic cell, a differential refractometer, a specific ion electrode, orr a spectrophotometer. Each of these detectors is capable of detecting and quantifying each ionic species of interest.

As noted above, a recorder 22 can be provided to receive and record electrical signals from conductivity cell 20.

Figure 2:
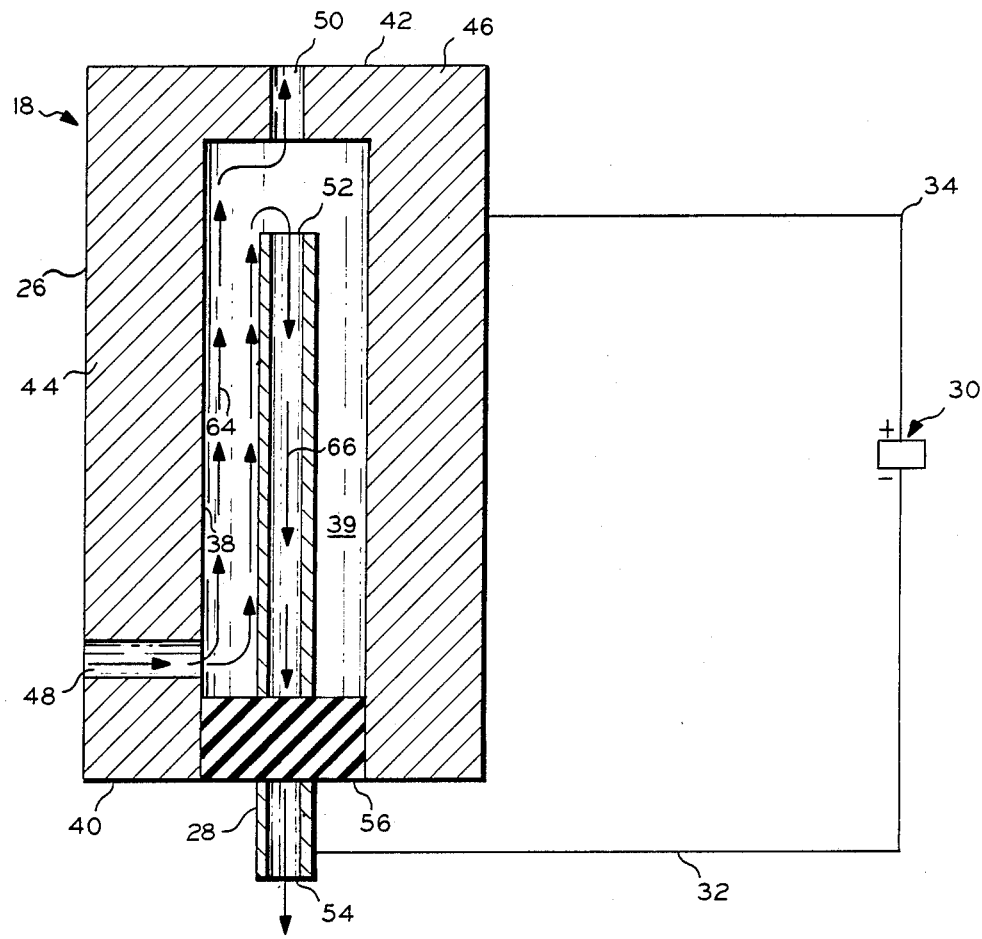
FIG. 2 is a cross-sectional view of the suppressor cell shown in FIG. 1. This FIGURE also shows an associated power source.

Referring now to FIG. 2, electrode 26 is essentially a hollow electrically conductive member which has an interior surface 38, which defines an interior space 39 therein, and also a first end 40 and a second end 42. Electrode 26 includes a sidewall 44 and an end wall 46 at end 42. Suppressor cell 18 also has an inlet 48 which is positioned near end 40 and which is defined by a passage through sidewall 44, and an outlet 50 positioned at end 42 and downstream from inlet 48 which is defined by a passage through end wall 46. As shown, inlet 48 and outlet 50 are in fluid communication with the space 39 defined within electrode 26.

Electrode 28 essentially comprises an electrically conductive tubular member, preferably coaxially mounted within electrode 26. Tubular electrode 28 has an open end 52 positioned within space 39 such that open end 52 is downstream from inlet 48 and in fluid communication with inlet 48, and an open end 54 which defines a second cell outlet. As shown, open ends 52 and 54 define the only openings in tubular electrode 28.

Electrodes 26 and 28 are most conveniently constructed of a machineable metal such as stainless steel. Surfaces which come into contact with fluid flow, which in the illustrated embodiment are the interior surface of electrode 26 and both the interior and exterior surfaces of electrode 28, are most commonly coated with a very thin inert metallic film. Either platinum or gold are suitable materials for such a film. Suppressor cell 18 also includes an electrically insulative member 56 having a suitably sized hole (not shown) for receiving tubular electrode 28 therethrough. As shown, insulative member 56 is sealingly engaged with a portion of the interior surface of electrode 26 and the exterior surface of electrode 28. The insulative member 56 therefore, serves to prevent fluid leakage from the cell and also serves to insulate electrode 26 from electrode 28.

A process which uses the apparatus shown in FIGS. 1 and 2 to analyze positively charged ionic species will now be described. For the sake of illustration, the eluting reagent will be assumed to be HCl, and the solvent pure water.

The eluting reagent HCl will become highly ionized in aqueous solution so as to form $H^+$ ions and $Cl^-$ ions. The eluant solution is drawn from eluant reservoir 10 by pump 12 and is passed through line 58 to sample injection valve 14. Thus, a continuous flow of eluant solution is passed through sample injection valve 14. Typical eluant solution flow rates fall, generally, in the range of about 20 to about 300 milliliters per hour when the separation column used has an inside diameter of a few millimeters.

A syringe is most conveniently employed to inject a portion of sample solution into sample injecting valve 14. The sample solution so injected measures out to typically no more than a few tenths of a milliliter of dilute solution containing a plurality of ionic species. The sample injection valve can then be manipulated as noted above such that eluant solution flowing through the valve sweeps the sample through line 60 and into separation column 16. It should be understood that other means of sample introduction may be employed, if desired, such as pipetting a sample into the top of separation column 16. However, gravity flow operations tend to be less easily controlled. Likewise the eluant solution could be added to separation column 16 manually as by pouring the solution into the open column, but is preferably added in a continuous stream to obtain better uniformity and reproducibility in results.

Various samples can be analyzed with the illustrated apparatus, such as industrial waste water. Covalent molecular compounds, such as amines, are often convertible to ionic form by making acid salts or quaternary ammonium compounds and thus analyzable by the apparatus.

The solution entering separation column 16 includes the ionized eluting reagent, which in this case comprises $H^+$ ions and $Cl^-$ ions, and ionic species all in solution. The ionic species in solution are carried accordingly through resin bed in column 16 by the eluant solution. An effluent is discharged by separation column 16 which includes $H^+$ ions, $Cl^-$ ions and separated ionic species. The effluent accordingly passes through line 62 and into suppressor cell 18.

An electrical voltage is applied to electrodes 26 and 28 by power source 30. For the purposes of cationic species detection, electrode 26 is maintained at a positive polarity, and electrode 28 is maintained at a negative polarity. Typically, the applied voltage is between about 1.2 and about 2.0 volts. Current density (current per unit surface area of the electrodes) typically ranges between about 0.01 and about 0.1 amps/cm². Therefore, an electric field is generated by the electrodes with a current flow that controls the amount of neutralization of certain eluant ions, discussed below, once a minimum applied voltage level is obtained.

Effluent from separation column 16 is received through cell inlet 48 via line 62 so as to flow along and in contact with the interior surface 38 of electrode 26 and the exterior and interior surfaces of electrode 28. The $Cl^-$ eluant ions in the effluent tend to be attracted to interior surface 38 of positive electrode 26. Thus, the $Cl^-$ eluant ions flow in solution along and closely adjacent to the interior surface 38. An electrolysis reaction also occurs at the interior surface of electrode 26, wherein water, which is the solvent, is broken down into $O_2$ and $H^+$ ions. This reaction is set forth below.

$$2H_2O = O_2 + 4H^+ + 4e^- \qquad (1)$$

The $H^+$ ions generated according to the above reaction tend to be repelled from the interior surface of electrode 26, but this is offset to a great degree by the attraction of the $Cl^-$ eluant ions flowing along interior surface 38. Therefore, due to this effect of the $Cl^-$ eluant ions, and also due to the continuous flow through cell 18, a substantial portion of the $H^+$ ions generated at interior surface 38 never reach the exterior surface of electrode 28. The voltages employed are typically insufficient for the oxidation of $Cl^-$ eluant ions at electrode 26. Thus, a portion of the effluent fluid flowing along and closely adjacent to interior surface 38 of electrode 26 includes most of the $Cl^-$ eluant ions in the effluent fluid, these $Cl^-$ eluant ions being attracted to the positively charged electrode 26. This effluent fluid portion containing $Cl^-$ eluant ions, as well as a substantial portion of the $H^+$ ions generated at interior surface 38, is received through outlet 50, and is typically sent to waste where it is discarded. Oxygen firmed from the above cited reaction tends to form bubbles in the flowing effluent fluid. These gas bubbles can be vented from outlet 50 to the atmosphere, or can be collected as desired. Flow of effluent fluid closely adjacent to interior surface 38 is shown schematically by the series of arrows as shown for example at 64.

$H^+$ eluant ions in the flowing effluent fluid tend to be attracted to the negatively charged electrode 28 so as to flow closely adjacent to the exterior surface of the electrode. These $H^+$ eluant ions and a small portion of the $H^+$ ions generated at electrode 26 undergo the following reaction at electrode 28:

$$2H^+ + 2e^- = H_2 \qquad (2)$$

As shown in equation (2), $H^+$ ions are reduced at electrode 28 to form hydrogen gas. Hydrogen gas bubbles are accordingly formed, a portion of which pass through outlet 50, and where the remainder pass through open end 52 of electrode 28. Thus, the $H^+$ eluant ions are neutralized by the cell. The above discussed range of voltages (i.e. between about 1.2 and about 2.0 volts) is typically sufficient to reduce the $H^+$ ions. However, the applied voltage to the electrode should be kept at as low a level as possible to perform the neutralization of the H+ ions, since excessively high voltages could cause ionic species flowing within the cell to enter into reaction. This, of course, is undesirable. Such a result depends to a large degree on the type of ionic species being analyzed. As used herein, the term "neutralization" is defined as the condition wherein ions are converted to an electrically neutral product. It should also be noted that if the voltage applied to the electrodes is kept in the range cited above, most ionic species being analyzed will not enter into reaction at the surfaces of the electrodes at these voltage levels.

Ionic species flowing from inlet 48 are positively charged and are therefore also attracted to the exterior surface of electrode 28 so as to flow along and closely adjacent to the exterior surface. Substantially all of the ionic species will adhere to the surface of the electrode 28 and reverse direction so as to flow along the interior surface of electrode 28 providing passage 50 is small enough to create a sufficient back pressure. In this regard, it is most convenient in actual practice to provide a flow restrictor means (not shown) such as a needle valve, whose flow area can be adjusted. The effluent portion flowing closely adjacent to surfaces of electrode 28 is schematically indicated by the series of arrows as shown at 66. Effluent fluid containing the separated ionic species consequently flows out lower open end 54.

The portion of the effluent fluid containing the ionic species flows from the open end or outlet 54 and through line 68 so as to be received by conductivity cell 20. Conductivity cell 20 detects the ionic species and produces an electrical signal in response thereto. This signal can be recorded by a recorder 22 as discussed above. Typically a series of peaks corresponding to the various ionic species will be obtained. Effluent fluid flowing out conductivity cell 20 is typically discarded.

As noted above, the H+ ions were substantially neutralized by the surface of electrode 28 such that fluid flowing into cell 20 contains substantially no eluant ions, or only a nominal amount of such eluant ions. Background noise is therefore substantially eliminated.

It should be noted that the two outlets of the suppressor cell in the illustrated embodiment, 50 and 54, are defined by the electrodes themselves. Therefore, these outlets are necessarily closely adjacent to surfaces of electrodes. However, it is within the scope of the invention to provide other electrode configurations, as long as they have surfaces along which effluent fluid flows, and wherein a cell outlet is provided for each electrode which is closely adjacent to and in fluid communication with an electrode surface. Such an arrangement permits ions flowing closely adjacent to the electrode surfaces to pass out of their respective outlets.

Figure 3:
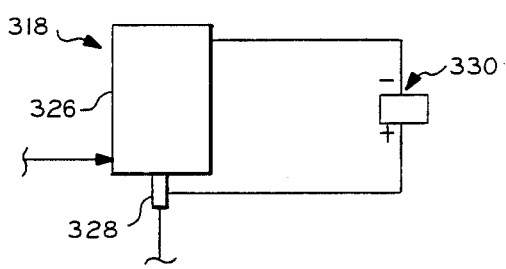
FIG. 3 illustrates a suppressor cell and associated power source for the detection of negatively charged ionic species.

Referring now to FIG. 3, a portion of an apparatus for the detection of negatively charged ionic species is shown. A suppressor cell 318 is illustrated which is substantially identical to the above described suppressor cell. A power source 330 is provided. Unlike the embodiment shown in FIG. 2, the negative terminal is connected to an electrode 326 which is generally similar to above described electrode 26. The positive terminal of power source 330 is connected to a tubular electrode 328 substantially similar to above described electrode 28. Thus the polarities are reversed in the FIG. 3 embodiment where negatively charged ionic species are being detected. Therefore, the negatively charged ionic species will tend to be attracted to the positive electrode 328 and flow through the interior passage defined therein to a conductivity cell where they are detected. In the embodiment in FIG. 3, certain other modifications would be made. For example, different eluting reagents would be used. Most preferably, the eluting reagent employed is a base, most preferably an alkali metal hydroxide such as NaOH, KOH, LiOH. NaOH is most preferred because it is relatively inexpensive. These types of eluting reagents are ionized in aqueous solution to yield a positively charged alkali metal ion and a negatively charged OH− ion. The positively charged alkali metal ions will pass through an outlet defined by electrode 326 similar to the above described outlet 50, and hydroxide ions will be oxidized by electrode 328 so as to form oxygen and water. Suitable ion exchange resins for use in the detection of negative ionic species include, for example, polystyrene carrying amine functional groups.

Thus, there is provided by the present invention a means of effectively minimizing background noise in the detection of ionic species by ion chromatography which does not require regeneration or replacement. Furthermore, since the ionic species are caused to flow closely adjacent to a surface of the one of the electrodes, this effectively limits the volume in which the ionic species flow (i.e., void volume). This minimization of void volume, as discussed above, serves to minimize band spreading.

Obviously many modifications and variations of the present invention are possible in light of the above teachings. It is therefore to be understood that within the scope of the appended claims the invention may be practiced otherwise than as specifically described.

That which is claimed is:

1. An apparatus for chromatographic analysis comprising:
   separation ion exchange resin bed means capable of separating a plurality of ionic species on being added to and eluted from such resin bed means with an eluant solution;
   means for introducing to said resin bed means a plurality of ionic species in solution and an eluant solution, wherein each ionic species is of a common first polarity, said first polarity being opposite to a second polarity, and wherein said eluant solution includes an eluting reagent in solution to form first eluant ions of said first polarity and second eluant ions of said second polarity, whereby an effluent consisting of separated ionic species and eluant ions is discharged from said resin bed means;
   an eluant ion suppressor cell which includes a first electrode, a second electrode, and a cell inlet for receiving effluent therethrough such that effluent flows along and in contact with a surface of said first electrode and a surface of said second electrode, said suppressor cell having a first outlet downstream from said cell inlet and closely adjacent to said first electrode surface so as to receive a portion of said effluent flowing closely adjacent to said first electrode surface, said cell also having a second cell outlet downstream from said cell inlet and closely adjacent to said second electrode surface so as to receive therethrough a portion of said effluent flowing closely adjacent to said second electrode surface;
   means for applying an electrical voltage to said first and second electrodes such that said first electrode is maintained at said first polarity and said second electrode is maintained at said second polarity, said voltage applying means being capable of applying a voltage sufficient to neutralize first eluant ions flowing along said second electrode;

detector means for receiving said portion of said effluent from said second outlet, said detector means detecting ionic species in said received effluent portion;

wherein one of said first and second electrodes comprises a hollow electrically conductive member having an interior surface which defines an interior space therein, said inlet being in fluid communication with said interior space such that said interior surface comprises the surface corresponding to said one electrode, and wherein the other of said first and second electrodes is disposed within said interior space; and wherein said other electrode comprises a tubular member which has a first open end, a second open end, and an exterior surface, said first open end being positioned within said interior space so as to be downstream from said cell inlet and in fluid communication therewith, and wherein said second open end defines said second outlet, and wherein the exterior surface of said tubular member comprises the surface corresponding to said other electrode.

2. An apparatus as recited in claim 1, wherein said tubular member is generally coaxially positioned with respect to said hollow member.

3. An apparatus as recited in claim 2, wherein said hollow member includes a wall, the cell outlet closely adjacent to said one electrode surface being defined by a passage through said wall, and wherein said hollow member also includes a wall having a passage therethrough which defines said cell inlet.

4. An apparatus as recited in claim 1, wherein said first and second open ends of said tubular member define the only openings in said tubular member.

5. An apparatus comprising:

a first hollow electrically conductive member having a first end, a second end, and an interior surface which defines an interior space therein, said first member including a wall with a first passage at said first end and a wall with a second passage near said second end, each of said passages being in fluid communication with said interior space; and a second electrically conductive tubular member generally coaxially positioned within said first member, and having two open ends, one of said ends being positioned in said space and in fluid communication with said first passage, and wherein said open ends define the only openings in said tubular member.

6. An apparatus as recited in claim 5, further comprising a means for applying an electrical voltage to said members.

* * * * *